(12) United States Patent
Mori

(10) Patent No.: US 11,686,318 B2
(45) Date of Patent: Jun. 27, 2023

(54) CENTRIFUGAL BLOOD PUMP DEVICE

(71) Applicant: TERUMO KABUSHIKI KAISHA, Tokyo (JP)

(72) Inventor: Takehisa Mori, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 599 days.

(21) Appl. No.: 16/750,098

(22) Filed: Jan. 23, 2020

(65) Prior Publication Data

US 2020/0155740 A1    May 21, 2020

Related U.S. Application Data

(63) Continuation of application No. PCT/JP2018/031492, filed on Aug. 27, 2018.

(30) Foreign Application Priority Data

Aug. 29, 2017   (JP) .............................. JP2017-164371

(51) Int. Cl.
*F04D 29/048*   (2006.01)
*F04D 1/00*   (2006.01)
(Continued)

(52) U.S. Cl.
CPC ......... *F04D 29/048* (2013.01); *A61M 60/148* (2021.01); *A61M 60/232* (2021.01);
(Continued)

(58) Field of Classification Search
CPC .............. A61M 60/422; A61M 60/148; A61M 60/419; A61M 60/824; A61M 60/232;
(Continued)

(56) References Cited

U.S. PATENT DOCUMENTS 4,763,032 A    8/1988   Bramm et al.
6,155,969 A *  12/2000  Schima ................ A61M 60/113
                                                           600/16

(Continued)

FOREIGN PATENT DOCUMENTS

JP        55-152916      11/1980
JP        2013213413 A   10/2013

OTHER PUBLICATIONS

Written Opinion of International Searching Authority, PCT/JP2018/031492, dated Nov. 13, 2018.
(Continued)

*Primary Examiner* — Peter J Bertheaud
(74) *Attorney, Agent, or Firm* — MacMillan, Sobanski & Todd, LLC

(57) ABSTRACT

A pump device (10) includes a housing (30) including a blood inflow port (38) through which blood flows in, and having a fixed-side repulsive magnet (44) disposed in an annular manner; and an impeller (14) that is rotatably housed inside the housing (30), and having a movable-side repulsive magnet (56) disposed in an annular manner. The fixed-side repulsive magnet (44) is disposed in a position offset toward the blood inflow port (38) side relative to the movable-side repulsive magnet (56). In the fixed-side repulsive magnet (44) and the movable-side repulsive magnet (56), a fixed-side repulsive surface (44a) and a movable-side repulsive surface (56a) adjacent to each other have the same polarity.

18 Claims, 6 Drawing Sheets

(51) Int. Cl.
| | |
|---|---|
| F04D 13/02 | (2006.01) |
| F04D 29/42 | (2006.01) |
| F16C 32/04 | (2006.01) |
| H02K 49/10 | (2006.01) |
| A61M 60/419 | (2021.01) |
| A61M 60/82 | (2021.01) |
| A61M 60/232 | (2021.01) |
| A61M 60/81 | (2021.01) |
| A61M 60/422 | (2021.01) |
| A61M 60/824 | (2021.01) |
| A61M 60/148 | (2021.01) |
| F04D 13/06 | (2006.01) |
| F04D 29/047 | (2006.01) |
| F04D 29/62 | (2006.01) |

(52) U.S. Cl.
CPC ........ *A61M 60/419* (2021.01); *A61M 60/422* (2021.01); *A61M 60/81* (2021.01); *A61M 60/82* (2021.01); *A61M 60/824* (2021.01); *F04D 1/00* (2013.01); *F04D 13/02* (2013.01); *F04D 13/024* (2013.01); *F04D 13/027* (2013.01); *F04D 13/0666* (2013.01); *F04D 29/047* (2013.01); *F04D 29/426* (2013.01); *F04D 29/628* (2013.01); *F16C 32/0474* (2013.01); *H02K 49/106* (2013.01)

(58) Field of Classification Search
CPC ..... A61M 60/81; A61M 60/82; F04D 29/048; F04D 29/047; F04D 13/027; F04D 13/026; F04D 13/0666; F04D 13/024; F04D 29/628; F04D 1/00; F04D 13/02; F04D 29/426; F16C 32/0474; H02K 49/106

See application file for complete search history.

(56) References Cited

U.S. PATENT DOCUMENTS

| | | | |
|---|---|---|---|
| 9,616,157 B2 * | 4/2017 | Akdis | ................ A61M 60/422 |
| 2010/0280305 A1 | 11/2010 | Hidaka et al. | |
| 2011/0238172 A1 | 9/2011 | Akdis | |

OTHER PUBLICATIONS

International Search Report, PCT/JP2018/031492, dated Nov. 13, 2018.

* cited by examiner

CENTRIFUGAL BLOOD PUMP DEVICE

CROSS REFERENCE TO RELATED APPLICATIONS

This application is a continuation of PCT Application No. PCT/JP2018/031492, filed Aug. 27, 2018, based on and claiming priority to Japanese Application No. 2017-164371, filed Aug. 29, 2017, both of which are incorporated herein by reference in their entirety.

BACKGROUND OF THE INVENTION

The present invention relates to a pump device that causes a fluid to flow.

A pump device is used as a blood circulation device that causes blood (fluid) to flow, in an artificial heart-lung apparatus having an oxygenator. For example, the pump device described in the description of US 2011/0238172 causes an impeller to rotate inside a housing, and by a centrifugal force with this rotation, leads blood into the housing, and discharges the blood from the housing.

In particular, the pump device described in US 2011/0238172 is provided with a bearing structure that inhibits the impeller from inclining in the radial direction when the impeller is rotating. The bearing structure includes a movable-side attracting magnet disposed to the impeller, and a fixed-side attracting magnet disposed to the housing in a further radially outer side than the movable-side attracting magnet. Further, in the fixed-side attracting magnet and the movable-side attracting magnet, mutually different polarities in the side surface cross-sectional view are caused to face to generate an attracting force therebetween, thereby inhibiting the inclination of the impeller.

Meanwhile, in the pump devices of this type, when the impeller rotates at high speed, some of the blood flows around to the lower side of the impeller, so that a back-side pressure is increased, which will cause the impeller to float. In particular, as in the description of US 2011/0238172, the configuration which includes the fixed-side attracting magnet and the movable-side attracting magnet easily causes the impeller to float. When this upward levitation force is large, the impeller may be brought into contact with a pump main body, which may cause a breakage, a lowering of the rotation speed, friction-induced destruction of blood cells, and so on.

SUMMARY OF THE INVENTION

The present invention has been made in view of the above circumstances, and one object thereof is to provide a pump device capable of rotating an impeller with stability by forming a bearing that can prevent the displacement of the impeller while inhibiting the inclination of the impeller using a simple configuration.

To attain these and other objects, a pump device according to the present invention includes: an impeller in which a first repulsive magnet is disposed in an annular manner; and a housing that rotatably houses therein the impeller, wherein the housing includes an internal space or chamber into which a fluid flows via an inlet port facing a rotation axis of the impeller, and in which a second repulsive magnet is disposed in an annular manner, wherein the second repulsive magnet is disposed in a position offset in the direction of the rotation axis toward the inlet port relative to the first repulsive magnet, and wherein the first repulsive magnet and the second repulsive magnet respectively have magnetic pole surfaces adjacent to each other with the same polarity.

With the above configuration, in the pump device, a repulsive force acts between magnetic pole surfaces adjacent to each other of the first repulsive magnet and the second repulsive magnet. In addition, the second repulsive magnet is disposed in a position offset in the direction of the rotation axis toward the inlet port relative to the first repulsive magnet (i.e., second repulsive magnet is above the first repulsive magnet), so that the second repulsive magnet applies a repulsive force in an opposite direction of the inlet port relative to the first repulsive magnet (i.e., downward). Accordingly, upward displacement of the impeller including the first repulsive magnet in a direction toward the inlet port is suppressed, so that the impeller can rotate with stability, thereby enabling the fluid to smoothly flow. For example, when the fluid is blood, it is possible to significantly inhibit the occurrence of thrombus and hemolysis.

In this case, the second repulsive magnet is preferably disposed in a position offset in a radial direction orthogonal to the rotation axis (e.g., radially outward) relative to the first repulsive magnet.

In the pump device, the second repulsive magnet is disposed in the position offset in the radial direction orthogonal to the rotation axis relative to the first repulsive magnet, so that the first repulsive magnet and the second repulsive magnet radially repel each other over the full circumference. This inhibits the inclination of the impeller in the radial direction, so that the impeller can rotate with stability.

Moreover, at least one of the first repulsive magnet and the second repulsive magnet may preferably be a ring body in which a first polarity is magnetized over an entire circumference of an outer circumferential portion (outer surface), and a second polarity that is an opposite polarity of the first polarity is magnetized over an entire circumference of an inner circumferential portion (inner surface).

In the pump device, the ring body in which the first polarity and the second polarity are respectively magnetized to the outer circumferential portion and the inner circumferential portion causes a repulsive force to be more uniformly generated along the circumference of the rotation axis of the impeller. This further increases the stability in the rotation of the impeller.

In addition, a drive device that receives the housing may preferably further be provided with a motor mechanism configured to rotate a driving magnet, and the impeller may preferably include a driven magnet that forms a magnetic coupling mechanism with the driving magnet, and is configured to rotate the impeller together with the rotation of the driving magnet.

The driving magnet and the driven magnet form the magnetic coupling mechanism, so that the pump device can transmit the torque of the driving magnet to the impeller in a non-contacting manner. This enables the inner space to be independent from the motor mechanism, and the displacement of the impeller in the radial direction and the direction toward the inlet port to be inhibited by the first repulsive magnet and the second repulsive magnet.

Here, a force obtained by adding a repulsive force between the first repulsive magnet and the second repulsive magnet to a magnetic coupling force of the magnetic coupling mechanism when the first repulsive magnet and the second repulsive magnet approach each other with a predetermined distance or less therebetween is preferably larger than a fluid force of the fluid.

The force obtained by adding the repulsive force to the magnetic coupling force is larger than the fluid force, so that the pump device can exhibit a large force when the first repulsive magnet and the second repulsive magnet approach each other with a predetermined distance or less therebetween, and can prevent the impeller from coming into contact with the housing even when rotating at high speed.

Further, the repulsive mechanism including the first repulsive magnet and the second repulsive magnet may preferably be disposed at a radially outward side (i.e., at a greater radial from the rotational axis) with respect to the driving/driven magnets of the magnetic coupling mechanism.

In the pump device, the repulsive mechanism is provided in a further radially outer side than the magnetic coupling mechanism, so that the first repulsive magnet and the second repulsive magnet are more easily designed independently of the driving/driven magnets, thereby enabling an appropriate repulsive force therebetween to be easily generated.

Moreover, the repulsive mechanism including the first repulsive magnet and the second repulsive magnet may preferably be provided closer to the side of the inlet port than the magnetic coupling mechanism.

The repulsive mechanism is provided to a position closer to the side of the inlet port than the magnetic coupling mechanism, so that the pump device can excellently inhibit the influence of the magnetic field of the magnetic coupling mechanism, and cause a repulsive force to act between the fixed-side repulsive magnet and the first repulsive magnet.

In addition, the first repulsive magnet and the second repulsive magnet respectively preferably have axial lengths (i.e., lengths parallel to the rotation axis) which are shorter than the axial lengths parallel to the rotation axis of the driving magnet and the driven magnet.

In the pump device, the axial lengths of the first repulsive magnet and the second repulsive magnet are short, so that it is possible to design the axial lengths of the impeller and the housing to be short. Therefore, the overall size of the entire device can be reduced.

Moreover, the housing includes a first housing including the impeller, and a second housing including the motor mechanism, and the first housing and the second housing may preferably be configured to be freely detachable.

In the pump device, the first housing and the second housing are freely detachable, so that while the impeller and the first housing are discarded after the use, the motor mechanism and the second housing can be reused.

In addition to the above configuration, the second repulsive magnet is preferably disposed in the first housing.

In the pump device, the second repulsive magnet disposed in the first housing can steadily push the first repulsive magnet of the impeller in the opposite direction of the inlet port. Accordingly, it is possible to reliably prevent the impeller from falling off from the bearing, when the pump device is transported.

With the present invention, the pump device is capable of rotating the impeller with stability by forming a bearing that can prevent the large displacement of the impeller while inhibiting the inclination of the impeller with a simple configuration.

DETAILED DESCRIPTION OF PREFERRED EMBODIMENTS

The following describes in details a preferred embodiment of a pump device according to the present invention with reference to the accompanying drawings.

Figure 1:
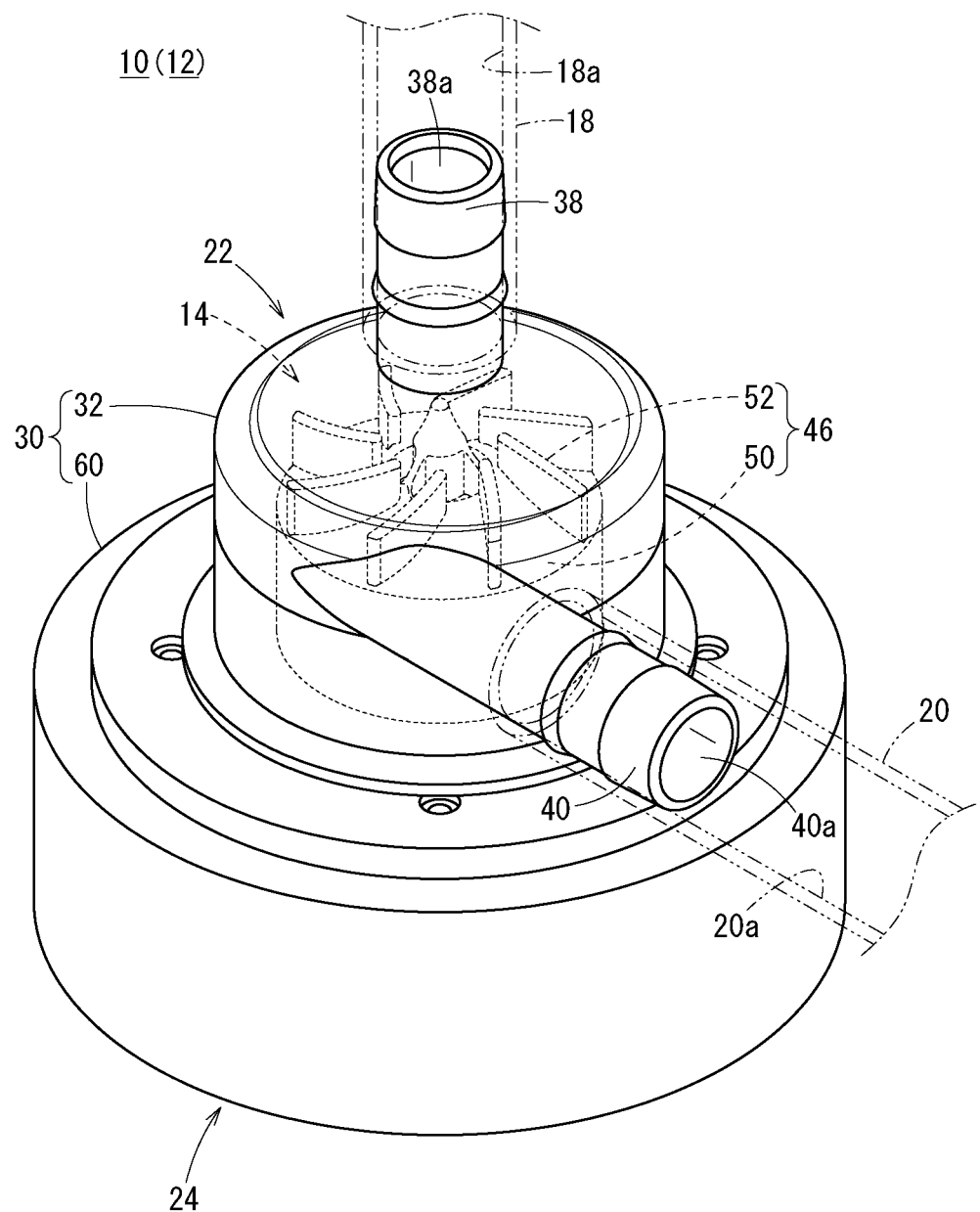
FIG. 1 is a perspective view of a pump device according to one embodiment of the present invention.

A pump device 10 according to one embodiment of the present invention is used, in an artificial heart-lung apparatus 12 that assists a cardiopulmonary function of a patient (or substitutes for the heart and the lungs), as a driving power source that removes blood from the patient to the outside of the body and transmits the blood to the inside of the body. As illustrated in FIG. 1, the pump device 10 includes an impeller 14 inside the device, and is configured as a centrifugal pump that causes the fluid to flow by a centrifugal force with the rotation of the impeller 14.

In the artificial heart-lung apparatus 12, a blood removal tube 18 and a blood transmission tube 20 are connected to the pump device 10 to form a circulation circuit with a patient, in which the blood is circulated. The blood removal tube 18 includes therein a blood removal lumen 18a with a tip opening that is indwelled in a desired living body organ (for example, left ventricle of a heart), and causes the blood of the patient to be aspirated through the blood removal lumen 18a. The blood transmission tube 20 includes therein a blood transmission lumen 20a with a tip opening that is indwelled in a desired living body organ (for example, subclavian artery), and causes the blood in the pump device 10 to be transmitted through the blood transmission lumen 20a. Note that, the artificial heart-lung apparatus 12 may have such a configuration that in addition to the pump device 10, a reservoir, an artificial lung, or the like (all of which are not illustrated) are connected within the circulation circuit (i.e., between the blood removal tube 18 and the blood transmission tube 20). This enables the artificial heart-lung apparatus 12 to perform the removal of foreign matters and the oxygenation on the blood removed to the outside of the body and to return the blood to the inside of the body of the patient.

Figure 2:
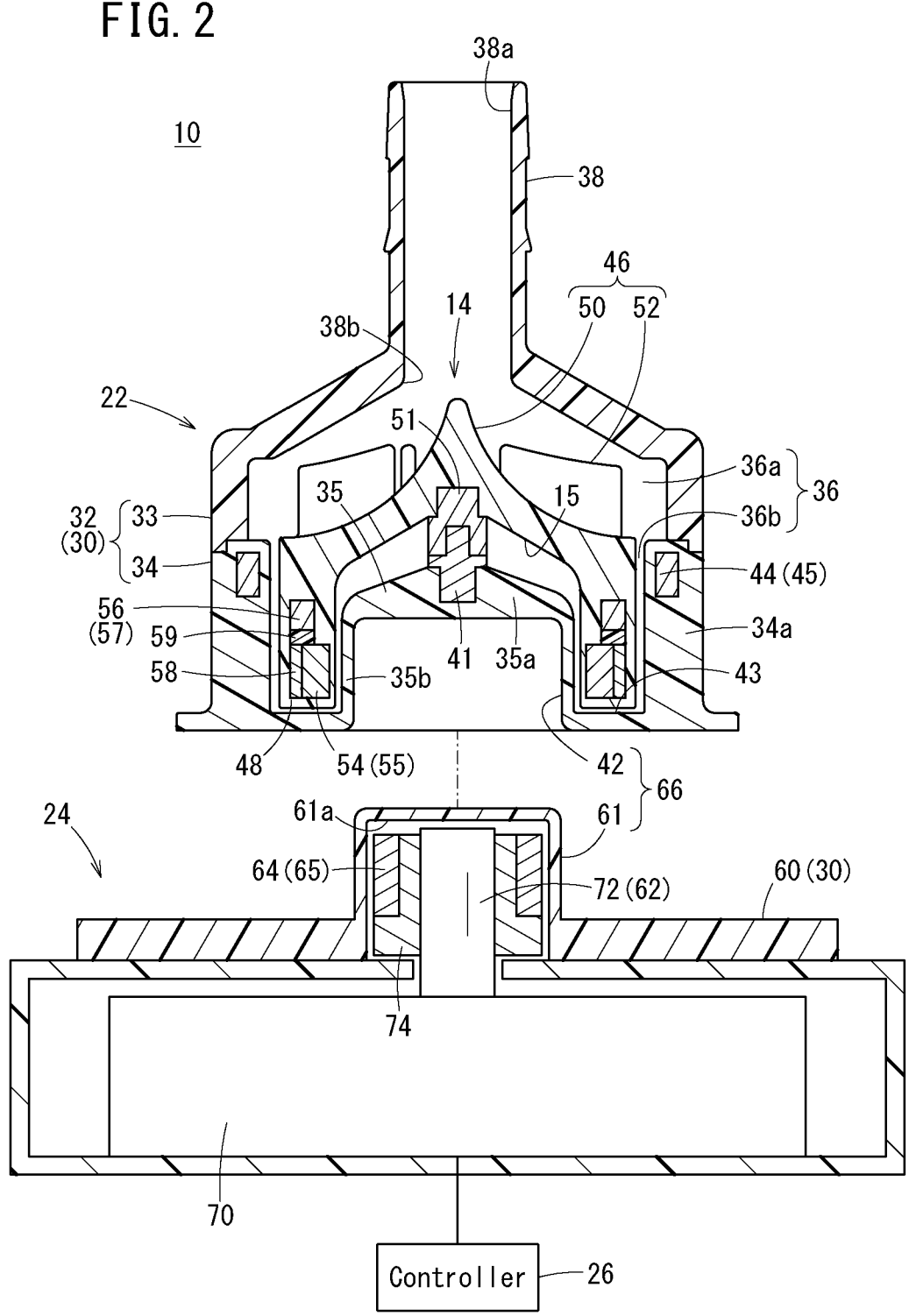
FIG. 2 is a side cross-sectional view illustrating a state where a pump main body and a drive device in FIG. 1 are separated from each other.

Further, as illustrated in FIG. 2, the pump device 10 according to the present embodiment includes a pump main body 22 in which the impeller 14 is housed, a drive device 24 that rotates the impeller 14, and a controller 26 that controls the drive of the drive device 24. Moreover, a housing 30 of the pump device 10 includes a main body side housing 32 (first housing) that includes the pump main body 22, and a drive side housing 60 (second housing) that includes the drive device 24.

In the housing 30, the main body side housing 32 and the drive side housing 60 are configured to be freely detachable, and are assembled to each other in use, thereby enabling a driving force of the drive device 24 to be transmitted to the impeller 14. After the use, the pump main body 22 is removed from the drive device 24 and discarded. In other words, the pump main body 22 is configured as a disposable type in which the pump main body 22 is replaced for every single use, and is expendable or subjected to sterilization processing. On the other hand, the drive device 24 is configured as a reuse type in which in a next use occasion, a new pump main body 22 is attached thereto, and the drive device 24 causes the impeller 14 of this pump main body 22 to operate.

The main body side housing 32 of the pump main body 22 is formed in a configuration that allows the pump main body 22 to be mounted to the drive device 24. Inside the main body side housing 32, the impeller 14 is rotatably housed, and an inner space or chamber 36 is formed, into and from which the blood flows.

As illustrated in FIG. 1 and FIG. 2, the main body side housing 32 includes a substantially conical upper housing portion 33, and a tubular lower housing portion 34 that is continuous to a lower part of the upper housing portion 33 and is mounted to the drive device 24. The inner space 36 is formed across both of the upper housing portion 33 and the lower housing portion 34. The upper housing portion 33 and the lower housing portion 34 are configured so as to be mutually separable to allow the impeller 14 to be taken out.

The upper housing portion 33 includes a blood inflow port 38 to be connected to the blood removal tube 18, and a blood outflow port 40 to be connected to the blood transmission tube 20. The blood inflow port 38 is provided in the center of a ceiling part of the upper housing portion 33, and protrudes in an upward direction, and in an inside thereof, an inflow path 38a that communicates with the inner space 36 of the upper housing portion 33 (hereinafter, referred to as a top space 36a) is provided. An inlet port 38b of blood is provided in a boundary between the inflow path 38a and the top space 36a. The blood outflow port 40 protrudes in a tangential direction from a side part of the top space 36a, and in an inside thereof, an outflow path 40a that communicates with the top space 36a is provided.

The top space 36a has a shape in accordance with the shape of the upper housing portion 33, and is formed so as to have a prescribed volumetric capacity. In the top space 36a, an upper-side fin portion 46 of the impeller 14 is disposed. In the center part of a bottom wall in a wall portion that surrounds the top space 36a, an axial support portion 35a of the lower housing portion 34 that supports the impeller 14 is provided.

The lower housing portion 34 protrudes in a downward direction of the upper housing portion 33, and is formed in a cylindrical shape having an axial center that is coaxial with the center of the top space 36a. A cylindrical tube portion 35 forms a hub that pivotally supports the impeller 14 is provided in the lower housing portion 34 at a center side thereof. The tube portion 35 includes the axial support portion 35a, and an inner circumferential portion 35b that is continuous with a circumferential edge and a lower side of the axial support portion 35a, and in an inside thereof, an insertion hole 42 that is open at a lower end side thereof is formed.

The center of the axial support portion 35a is overlapped with a rotation axis O of the impeller 14, and a support member 41 made of metal is provided therein. The support member 41 protrudes from the axial support portion 35a toward a direction of the inlet port 38b, and rotatably and pivotally supports the impeller 14 from an inner side.

Moreover, in an inside of the lower housing portion 34, a lower space 36b (a part of the inner space 36) that communicates with the top space 36a is formed. The lower space 36b radially encircles the side of the insertion hole 42 in accordance with the cylindrical shape of the lower housing portion 34, and rotatably houses a driven rotation structure portion 48 of the impeller 14. In a bottom portion that configures the lower space 36b, a dynamic-pressure bearing 43 that rotates the impeller 14 in a non-contacting manner (dynamic-pressure bearing in a thrust direction) is provided. For example, a groove having a predetermined shape and a shallowly cut-out bottom portion can be utilized as the dynamic-pressure bearing 43.

Further, the pump device 10 according to the present embodiment includes a fixed-side repulsive magnet 44 (second repulsive magnet) in an outer circumferential portion 34a on a radially outer side of the lower housing portion 34. The fixed-side repulsive magnet 44 is embedded in the outer circumferential portion 34a, and cooperates with a later-described movable-side repulsive magnet 56 to form a repulsive mechanism 78 in which the fixed-side repulsive magnet 44 and the movable-side repulsive magnet 56 repel each other.

Figure 3:
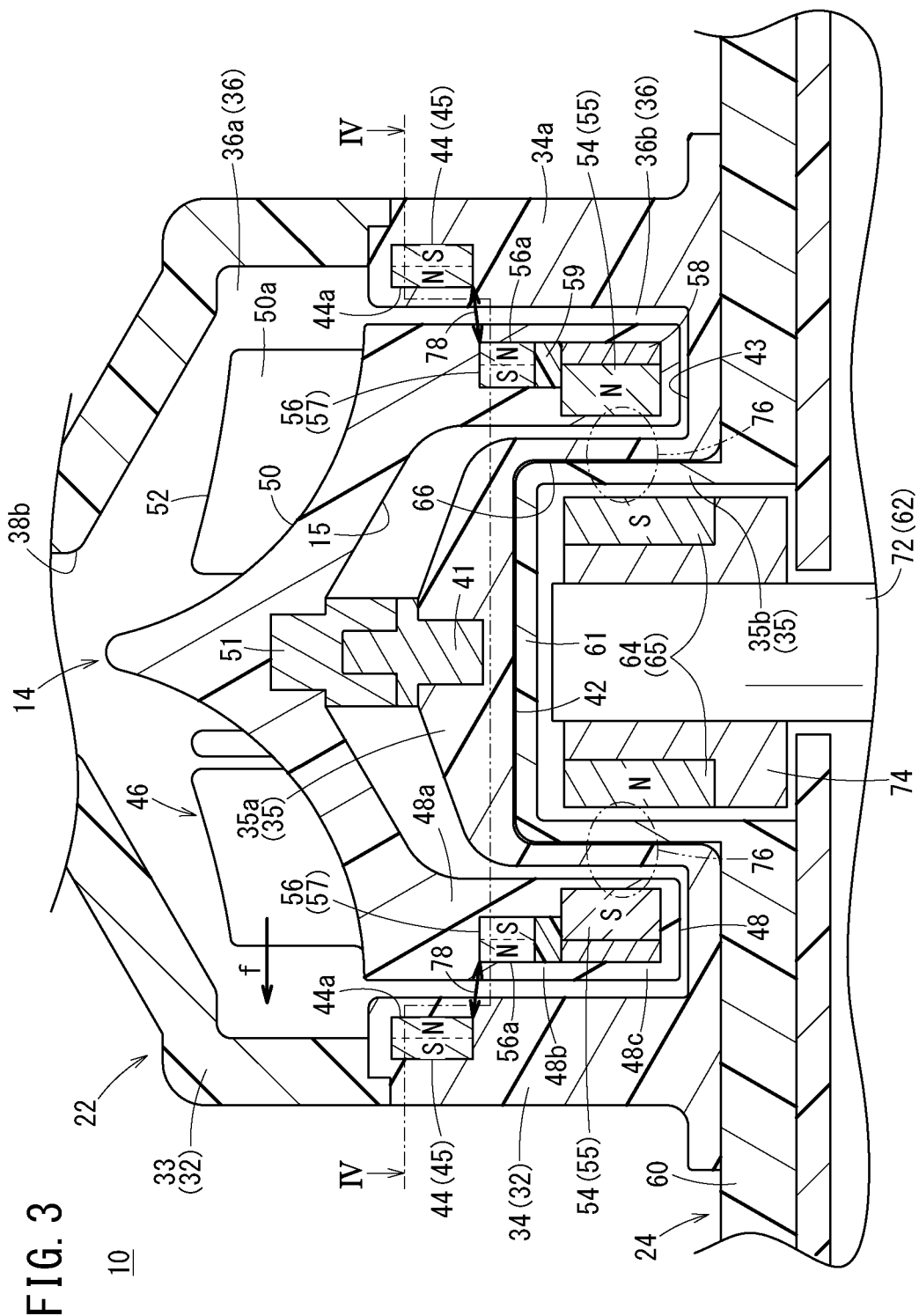
FIG. 3 is a side cross-sectional view illustrating a relevant portion of the pump device in greater detail.
Figure 4:
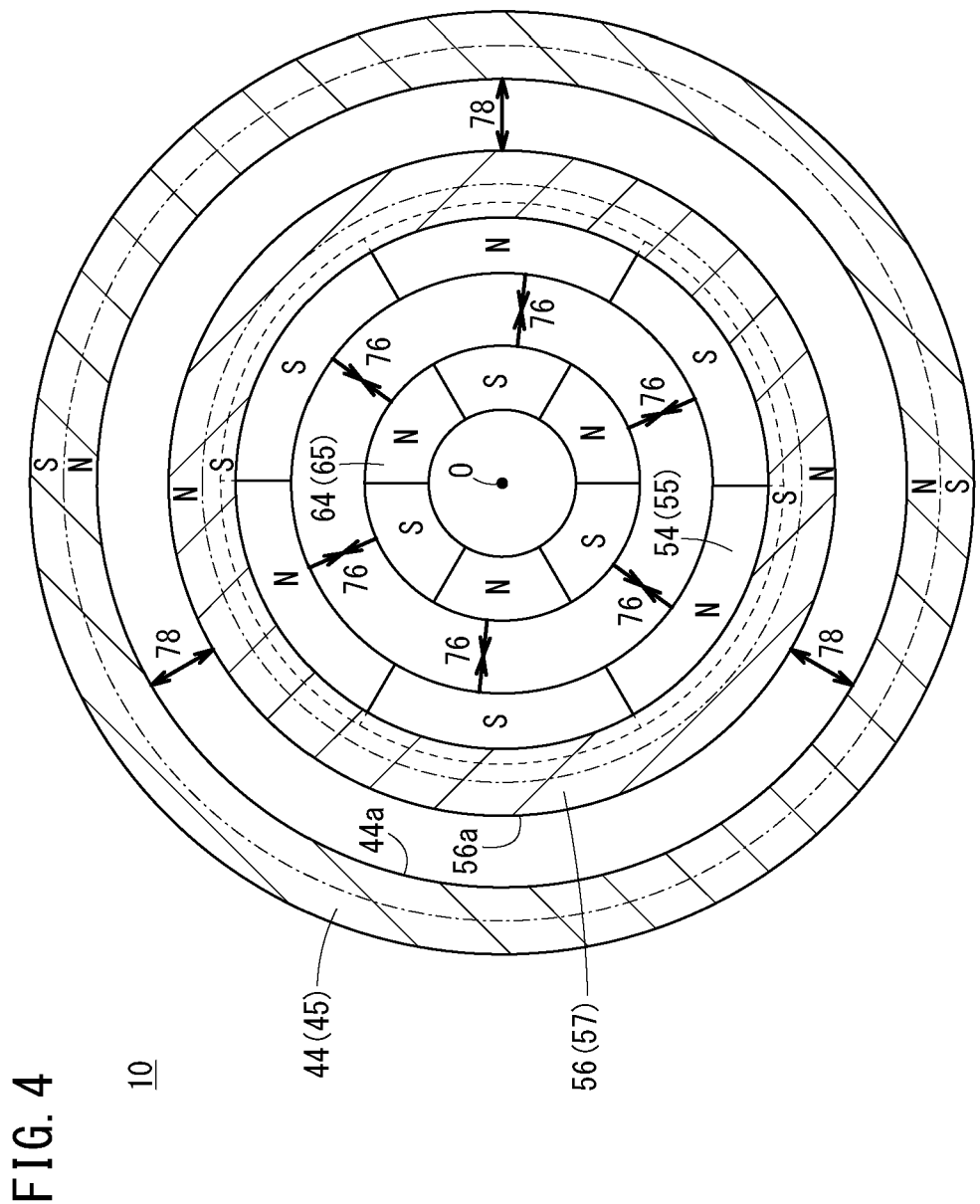
FIG. 4 is a cross-sectional view taken along the line IV-IV in FIG. 3, illustrating a driven magnet, a movable-side repulsive magnet, a drive magnet, and a fixed-side repulsive magnet.

As illustrated in FIG. 2 and FIG. 3, the fixed-side repulsive magnet 44 is configured in a fixed-side inner-outer circumferential single-polar magnetization ring magnet 45 that follows a circular path at a position farthest from the rotation axis O of the impeller 14. As illustrated in FIG. 4, the fixed-side inner-outer circumferential single-polar magnetization ring magnet 45 is a ring body that is magnetized so as to have a first polarity (S pole in FIG. 4) over the entire circumference of an outer circumferential portion (outer cylindrical surface), and have a second polarity (N pole in FIG. 4), which is opposite to the first polarity, over the entire circumference of an inner circumferential portion (inner cylindrical surface). In other words, an inner circumferential surface of the fixed-side repulsive magnet 44 is a fixed-side repulsive surface 44a (magnetic pole surface) in which the second polarity is always present along the circumferential direction.

Moreover, the fixed-side repulsive magnet 44 is disposed closer to an upper end (in the vicinity of the upper housing portion 33) of the cylindrical outer circumferential portion 34a. Accordingly, in a mounted state of the pump main body 22 and the drive device 24, the fixed-side repulsive magnet 44 is positioned at the most upper side (side of the inlet port 38b) relative to other magnets. The fixed-side repulsive surface 44a of the fixed-side repulsive magnet 44 faces an upper thick-wall portion 48a of the driven rotation structure portion 48 of the impeller 14.

Materials included in the fixed-side repulsive magnet 44 (the fixed-side inner-outer circumferential single-polar magnetization ring magnet 45) are not specially limited, and examples of the materials include hard magnetic materials, such as alnico, ferrite, and neodymium.

Referring back to FIG. 2 and FIG. 3, the impeller 14 is formed in an approximately conical shape having a cavity 15 in an inside thereof, and is housed in the main body side housing 32 so as to cover the axis tube portion 35. In the housed state, a slight gap is generated between a circumferential surface of the impeller 14 and a wall surface of the lower housing portion 34 (the outer circumferential portion 34a of the lower housing portion 34, the inner circumferential portion 35b of the axis tube portion 35). The interval of this gap is set, depending on the size of the pump main body 22, for example, to a range of 0.1 mm to 1 mm, approximately.

The impeller 14 includes the upper-side fin portion 46 in which a plurality of fins 52 protrude, and the driven rotation structure portion 48 that is continuous with a lower side of the fin portion 46. In other words, the impeller 14 is an open type impeller in which a flow path 50a formed between the respective fins 52 is exposed. Note that, the impeller 14 is not limited to the open type, may be configured as a close type in which a shroud (which is not illustrated) that cover the flow path 50a is provided.

The fin portion 46 is disposed in the top space 36a, and applies a centrifugal force to the blood with the rotation. The fin portion 46 includes a cone portion 50 that configures a bottom portion of the cavity 15, and the plurality of the fins 52 that respectively protrude from the cone portion 50. The plurality of the fins 52 are designed to have an inclination and a curved shape that allow an appropriate centrifugal force to be generated in accordance with the rotation state (rotation direction, rotation speed, and the like) of the impeller 14.

In an inner side part and a center part of the cone portion 50 that configures the cavity 15, a receiving member 51 to be put on the support member 41 is provided. The support structure of the support member 41 and the receiving member 51 causes the impeller 14 to freely rotate while the displacement in the downward direction being inhibited.

The driven rotation structure portion 48 is formed in a cylindrical shape having a thickness in the radial direction of the impeller 14, and rotates by a torque of the drive device 24 being transmitted thereto, in the mounted state of the pump main body 22 and the drive device 24, as illustrated in FIG. 2 and FIG. 3. In an inside of the driven rotation structure portion 48, a driven magnet 54 and the movable-side repulsive magnet 56 (first repulsive magnet) are mounted.

The driven magnet 54 is disposed in a lower thick-wall portion 48c of the driven rotation structure portion 48. The driven magnet 54 is aligned in the radial direction relative to a driving magnet 64 of the drive device 24, in the mounted state of the pump main body 22 and the drive device 24, and forms a magnetic coupling mechanism 76 with the driving magnet 64 therebetween.

As illustrated in FIG. 4, the driven magnet 54 is included in a driven side multi-polar magnetization ring magnet 55 that encircles the rotation axis O of the impeller 14 by a fixed radius. The driven side multi-polar magnetization ring magnet 55 is magnetized such that a plurality of N poles and S poles are alternately aligned along the circumferential direction. In FIG. 4, the number of poles in the driven side multi-polar magnetization ring magnet 55 is designed to be six (in other words, three counter electrodes), but is not limited thereto. Materials included in the driven magnet 54 (the driven side multi-polar magnetization ring magnet 55) are not specially limited, and the materials having been described as for the fixed-side repulsive magnet 44 can be applied. Moreover, on an outer circumferential surface side of the driven magnet 54, a back yoke 58 is disposed over the entire circumference in the circumferential direction. For example, the back yoke 58 includes a material that inhibits the transmission of a magnetic force.

Meanwhile, as illustrated in FIG. 3 and FIG. 4, the movable-side repulsive magnet 56 is disposed in an intermediate side thick-wall portion 48b of the driven rotation structure portion 48, which is above the driven magnet 54. Between the driven magnet 54 and the movable-side repulsive magnet 56, a back yoke 59 that inhibits the transmission of a magnetic force is interposed.

As described above, the movable-side repulsive magnet 56 forms the repulsive mechanism 78 in which the movable-side repulsive magnet 56 and the fixed-side repulsive magnet 44 repel each other. As illustrated in FIG. 4, the movable-side repulsive magnet 56 is configured in a movable-side inner-outer circumferential single-polar magnetization ring magnet 57 that revolves at a position distant from the rotation axis O by a predetermined distance. The movable-side inner-outer circumferential single-polar magnetization ring magnet 57 is a ring body that is magnetized so as to have a first polarity (N pole in FIG. 4) over the entire circumference of an outer circumferential portion, and have a second polarity (S pole in FIG. 4), which is opposite to the first polarity, over the entire circumference of an inner circumferential portion. In other words, an outer circumferential surface of the movable-side repulsive magnet 56 is a movable-side repulsive surface 56a (magnetic pole surface) in which the same polarity as that of the fixed-side repulsive surface 44a of the fixed-side repulsive magnet 44 is always present along the circumferential direction.

Moreover, an axial length (thickness of the movable-side repulsive magnet 56) of the movable-side repulsive magnet 56 (the movable-side inner-outer circumferential single-polar magnetization ring magnet 57) parallel to the rotation axis O is shorter than an axial length of the driven magnet 54. In addition, the axial length of the movable-side repulsive magnet 56 is designed to be shorter than the axial length of the fixed-side repulsive magnet 44. Materials included in the movable-side repulsive magnet 56 are not specially limited either, and the materials having been described as for the fixed-side repulsive magnet 44 can be applied.

In addition, an arrangement state of the fixed-side repulsive magnet 44 and the movable-side repulsive magnet 56 will be described. Specifically, the fixed-side repulsive magnet 44 is disposed at a position offset toward a blood inflow side (side of the inlet port 38b) relative to the movable-side repulsive magnet 56. In other words, the fixed-side repulsive magnet 44 and the movable-side repulsive magnet 56 are basically disposed along the radial direction orthogonal to the rotation axis O so as not to face each other, and on the other hand, the fixed-side repulsive surface 44a and the movable-side repulsive surface 56a that are adjacent to each other have the same polarity.

The offset amount of the fixed-side repulsive magnet 44 and the movable-side repulsive magnet 56 is not specially limited, but, for example, a lower end (adjacent end) of the fixed-side repulsive magnet 44 and an upper end (adjacent end) of the movable-side repulsive magnet 56 may preferably be apart from within a range of several micrometers to several millimeters. Accordingly, the fixed-side repulsive magnet 44 and the movable-side repulsive magnet 56, even when being offset in the direction of the rotation axis O, mutually exhibit a repulsive force therebetween excellently.

Accordingly, the fixed-side repulsive magnet 44 pushes down the movable-side repulsive magnet 56 into the radially inner side and the downward direction (opposing side from the inlet port 38b). In other words, the repulsive mechanism 78 forms a bearing in the radial direction (radial direction) and a bearing in the thrust direction (upward direction), and any inclination in the radial direction (i.e., misalignment between the rotational axis of the impeller 14 and the central axis of main body 22) and upward displacement to the side of the inlet port 38b of the impeller 14 including the movable-side repulsive magnet 56 are inhibited. In other words, the arrangement orients the repulsive force acting on the impeller 14 with components directed both radially inward and vertically downward which is applied around the full circumference of the impeller 14.

Further, the repulsive mechanism 78 is included only in the pump main body 22, and therefore also inhibits, when the pump main body 22 is transported, the impeller 14 from displacing to the side of the inlet port 38b inside the main body side housing 32. In particular, the impeller 14 according to the present embodiment has a configuration of being pivotally supported by the support member 41 on which the receiving member 51 in the center part is put, and therefore, the repulsive mechanism 78 can prevent the impeller 14 from falling off from the support member 41 by the displacement of the impeller 14.

Meanwhile, as illustrated in FIG. 2 and in FIG. 3, the drive device 24 of the pump device 10 includes the drive side housing 60, and a motor mechanism 62 that is housed inside the drive side housing 60. In addition, the drive device 24 includes the driving magnet 64 that is provided to the motor mechanism 62, and configures the magnetic coupling mechanism 76 with the impeller 14 therebetween.

The drive side housing 60 configures a mutually freely detachable engagement structure 66 with the main body side housing 32 of the pump main body 22. For example, the engagement structure 66 includes the inner circumferential portion 35*b* of the lower housing portion 34 that surrounds the insertion hole 42, and a central convex portion 61 of the drive side housing 60 to be inserted into the insertion hole 42, and can have a structure in which positioning and fitting are firmly performed in a state where the central convex portion 61 is inserted into the insertion hole 42. Note that, it is needless to say that the engagement structure 66 may employ various kinds of configurations.

An inner side of the central convex portion 61 is a space portion 61*a* in which an axis portion 72 of the motor mechanism 62 is housed. The motor mechanism 62 includes a motor main body 70 that is covered with the drive side housing 60 and fixed with a screw. The motor main body 70 rotates the axis portion 72 at an appropriate rotation speed under the control of the controller 26.

The axis portion 72 protrudes from the motor main body 70 into the space portion 61*a*, and holds the driving magnet 64 with a fixing member 74 inside the space portion 61*a*. An axial center (rotation axis O) of the axis portion 72 in the mounted state of the pump main body 22 and the drive device 24 is overlapped with the rotation axis O of the impeller 14. The fixing member 74 is formed in a cylindrical shape, and secures the driving magnet 64 at a predetermined height position on an outer circumferential surface thereof.

As illustrated in FIG. 4, the driving magnet 64 according to the present embodiment is configured in a drive side multi-polar magnetization ring magnet 65 that encircles the rotation axis O of the axis portion 72 by a radius shorter than that of the driven magnet 54. The drive side multi-polar magnetization ring magnet 65 is magnetized such that a plurality (six) of poles (N poles and S poles) are alternately disposed along the circumferential direction, similarly to the driven magnet 54.

In addition, an axial length of the driving magnet 64 parallel to the rotation axis O is formed to be longer than that of the driven magnet 54, and an upper end of the drive magnet 64 reaches in the vicinity of a side of a ceiling part of the central convex portion 61. This enables, in the mounted state of the pump main body 22 and the drive device 24, the driven magnet 54 and the driving magnet 64 to be aligned in the radial direction, and the magnetic coupling mechanism 76 to be excellently formed. Moreover, also as for materials included in the driving magnet 64, the materials having been described as for the fixed-side repulsive magnet 44 can be selected as appropriate.

Referring back to FIG. 2, the controller 26 of the pump device 10 is configured by a well-known computer that includes input and output interfaces, a memory, and a processor, which are not illustrated, and controls the drive of the motor mechanism 62. On an outer surface of the controller 26, a monitor, a speaker, operation buttons, and the like, which are not illustrated, are provided, a user such as a medical doctor or a nurse operates the operation button to set the drive content of the pump device 10. The controller 26 controls the supply of electric power to a battery on the basis of setting information by the user, and rotates the axis portion 72 within a range of 0 to 80000 rpm, for example.

Next, an effect by the pump device 10 having the above-described configuration will be described.

The artificial heart-lung apparatus 12 including the pump device 10 is constructed to a patient whose cardiopulmonary function is to be assisted. When the artificial heart-lung apparatus 12 is constructed, a user connects the blood removal tube 18 and the blood transmission tube 20 to the prepared pump main body 22. Subsequently, as illustrated in FIG. 2, the pump main body 22 is mounted relative to the drive device 24, thereby assembling the pump device 10. At this time, the user inserts the central convex portion 61 of the drive side housing 60 into the insertion hole 42 of the main body side housing 32, and positions and fixes the pump main body 22 and the drive device 24 to each other.

Here, the fixed-side repulsive magnet 44 (the fixed-side inner-outer circumferential single-polar magnetization ring magnet 45) and the movable-side repulsive magnet 56 (the movable-side inner-outer circumferential single-polar magnetization ring magnet 57) of the pump main body 22 form the repulsive mechanism 78 in which adjacent surfaces repel each other with the same polarity. The fixed-side repulsive magnet 44 is located above the movable-side repulsive magnet 56 (offset position), and applies a repulsive force to the movable-side repulsive magnet 56 toward the radially inner side and the downward direction. Therefore, the repulsive mechanism 78 inhibits, when the pump main body 22 is being transported, the impeller 14 from taking out from the support member 41, thereby implementing the support with stability.

Moreover, as illustrated in FIG. 3, in the mounted state, the driven magnet 54 and the driving magnet 64 are aligned in the radial direction orthogonal to the rotation axis O. Therefore, the driven magnet 54 (the driven side multi-polar magnetization ring magnet 55) and the driving magnet 64 (the drive side multi-polar magnetization ring magnet 65) with different polarities face each other to form the magnetic coupling mechanism 76. In other words, the driven side multi-polar magnetization ring magnet 55 and the drive side multi-polar magnetization ring magnet 65 cause a magnetic coupling force to be generated, and allow a torque of the axis portion 72 to be transmitted to the impeller 14.

Accordingly, when the motor mechanism. 62 of the drive device 24 rotates the axis portion 72, the impeller 14 also concomitantly rotates. Further, the fin portion 46 that rotates inside the top space 36*a* causes a centrifugal force to be generated, and thus flows blood sequentially through the inflow path 38*a*, the inner space 36, the flow path 50*a*, and the outflow path 40*a*.

The impeller 14, when being rotating, rotates in a non-contact manner relative to a bottom portion of the main body side housing 32 by the dynamic-pressure bearing 43 in the thrust direction. Moreover, the repulsive mechanism 78 formed by the fixed-side repulsive magnet 44 and the movable-side repulsive magnet 56 generates a repulsive force uniformly above the magnetic coupling mechanism 76 and in the entire circumferential direction to form a bearing in the radial direction and a bearing in the thrust direction (upward direction).

Here, a floating force in the thrust direction by a fluid force f (an inflow pressure force and an outflow pressure force: back-side pressure force) of blood acts on the impeller 14 when being rotating at a high speed and other cases. However, even when the impeller 14 floats from a support position by the support member 41, a distance between the fixed-side repulsive magnet 44 and the movable-side repulsive magnet 56 becomes closer, and the repulsive mechanism 78 applies a large repulsive force. In particular, the pump device 10 is designed in advance such that a force obtained by adding the magnetic coupling force of the magnetic coupling mechanism 76 to the repulsive force of the repulsive mechanism 78 is larger than the fluid force f of the blood. Accordingly, it is possible to inhibit the impeller 14 from moving upward.

Moreover, when the impeller 14 rotates, together with the magnetic coupling mechanism 76 and the fluid force f of the blood, a force to incline the impeller 14 in the radial direction may be applied relative to the axis tube portion 35 in some cases. To cope with this, the repulsive mechanism 78 causes the impeller 14 to immediately return to an original posture by the repulsive force between the fixed-side repulsive magnet 44 and the movable-side repulsive magnet 56, and effectively inhibits the impeller 14 from coming into contact with the main body side housing 32. Accordingly, the pump device 10 can steadily and stably drive the impeller 14 to excellently obtain a centrifugal force, and can cause the blood to smoothly flow in the artificial heart-lung apparatus 12.

As described above, the pump device 10 according to the present embodiment exhibits the following effects.

In the pump device 10, a repulsive force acts between the fixed-side repulsive surface 44a of the fixed-side repulsive magnet 44 and the movable-side repulsive surface 56a of the movable-side repulsive magnet 56. In addition, the fixed-side repulsive surface 44a is disposed at a position offset toward the inlet port 38b relative to the movable-side repulsive surface 56a, so that the fixed-side repulsive magnet 44 applies a repulsive force in an opposite direction of the inlet port 38b relative to the movable-side repulsive magnet 56. This inhibits the inclination in the radial direction and the displacement in a direction toward the inlet port 38b of the impeller 14 including the movable-side repulsive magnet 56, so that the impeller 14 can rotate with stability, thereby enabling the blood to smoothly flow. For example, it is possible to significantly inhibit the occurrence of thrombus and hemolysis.

In this case, because the fixed-side repulsive magnet 44 and the movable-side repulsive magnet 56 are respectively the fixed-side inner-outer circumferential single-polar magnetization ring magnet 45 and the movable-side inner-outer circumferential single-polar magnetization ring magnet 57, the pump device 10 causes a repulsive force to be more uniformly generated along the circumference of the rotation axis of the impeller 14. This further increases the stability in the rotation of the impeller 14.

In particular, the driven magnet 54 and the driving magnet 64 form the magnetic coupling mechanism 76, so that the pump device 10 can transmit a torque of the driving magnet 64 to the impeller 14 in a non-contact manner. This enables the inner space 36 to be independent from the motor mechanism 62, and the repulsive mechanism 78 to inhibit the displacement in the radial direction and to the side of the inlet port 38b. Moreover, the pump device 10 is designed to have the force obtained by adding the repulsive force to magnetic coupling force being larger than the fluid force f. Accordingly, the fixed-side repulsive magnet 44 and the movable-side repulsive magnet 56 approach each other with a predetermined distance or less therebetween to exhibit a larger force, thereby enabling the impeller 14 to be immediately returned to the original posture.

In addition, in the pump device 10, the repulsive mechanism 78 is provided in a further radially outer side than the magnetic coupling mechanism 76, so that the fixed-side repulsive magnet 44 and the movable-side repulsive magnet 56 are easily designed, thereby enabling an appropriate repulsive force therebetween to be easily generated. The repulsive mechanism 78 is provided to a position closer to the side of the inlet port 38b than the magnetic coupling mechanism 76, so that the pump device 10 can excellently inhibit the influence of the magnetic field of the magnetic coupling mechanism 76.

Moreover, in the pump device 10, the axial lengths of the fixed-side repulsive magnet 44 and the movable-side repulsive magnet 56 are short, so that it is possible to design the axial lengths of the impeller 14 and the housing 30 to be short. Therefore, the downsizing of the entire device can be made. Further, in the pump device 10, with the fixed-side repulsive magnet 44 disposed to the pump main body 22, it is possible to steadily push the movable-side repulsive magnet 56 of the impeller 14 in an opposite direction of the blood inflow port 38. Accordingly, it is possible to prevent the impeller 14 from falling off from the support member 41, when the pump main body 22 is transported.

Note that, the pump device 10 according to the present invention is not limited to the above embodiment, but various kinds of application examples and modification examples can be employed. For example, the pump device 10 is configured such that the pump main body 22 and the drive device 24 can be assembled freely detachable, but is not limited thereto. The pump device 10 may be a device in which the pump main body 22 and the drive device 24 are integrated, in other words, may have an integrated housing 30.

Hereinafter, modification examples of the pump device 10 according to the present invention will be described. Note that, in the following explanation, a configuration having the same configuration or the same function as that of the above-described pump device 10 is assigned with the same reference numeral, and a detailed explanation thereof is omitted.

First Modification Example

Figure 5:
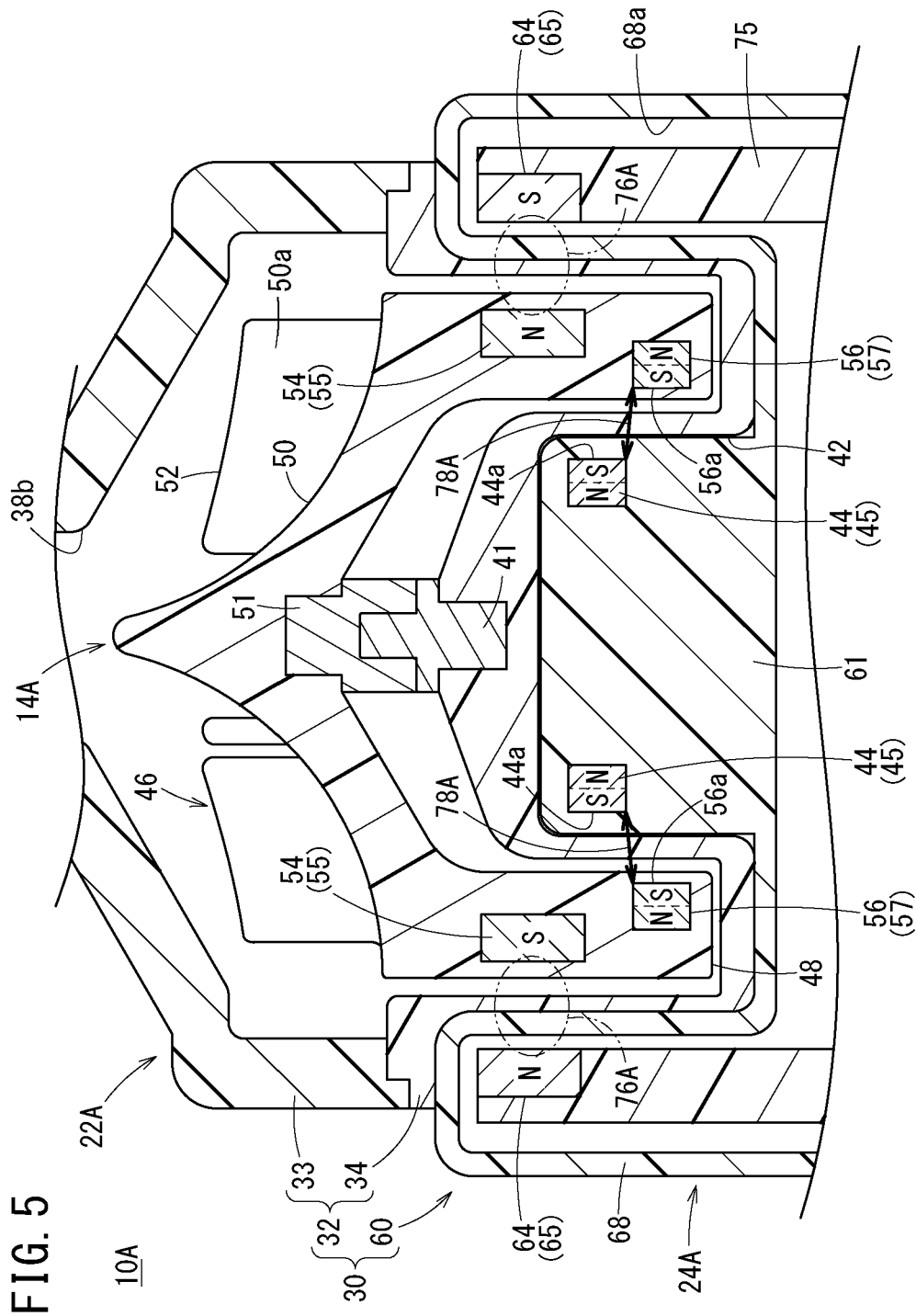
FIG. 5 is a side cross-sectional view illustrating a relevant portion of a pump device according to a first modification example.

A pump device 10A according to a first modification example illustrated in FIG. 5 is different from the pump device 10 in that a repulsive mechanism 78A for stabilizing the impeller is provided in a radially inner side and below a magnetic coupling mechanism 76A for driving the rotation of the impeller.

Specifically, an impeller 14A of the pump device 10A is provided with the driven magnet 54 (the driven side multi-polar magnetization ring magnet 55) on a radially outer side, and the movable-side repulsive magnet 56 (the movable-side inner-outer circumferential single-polar magnetization ring magnet 57) below and radially inside the driven magnet 54. The driven magnet 54 and the movable-side repulsive magnet 56 are disposed at a predetermined interval in a direction parallel to the rotation axis O.

Meanwhile, the drive side housing 60 of a drive device 24A is provided with a surrounding convex portion 68 that revolves with an interval around the central convex portion 61 to be inserted into the insertion hole 42 of a pump main body 22A. Moreover, a tubular rotor 75 is fixed to the axis portion 72 of the motor mechanism 62, and a radially outer side upper end of the rotor 75 is housed in a space portion 68a of the surrounding convex portion 68. Further, the driving magnet 64 (the drive side multi-polar magnetization ring magnet 65) is secured to the radially outer side upper end of the rotor 75.

Moreover, in an inside of the central convex portion 61, the fixed-side repulsive magnet 44 (the fixed-side inner-outer circumferential single-polar magnetization ring magnet 45) is embedded. The fixed-side repulsive magnet 44 and the movable-side repulsive magnet 56 are disposed, in an assembled state of the pump main body 22A and the drive device 24A, in offset positions in a direction along the rotation axis O, and the fixed-side repulsive magnet 44 is present closer to the inlet port 38b than the movable-side repulsive magnet 56.

In the pump device 10A described above, the fixed-side repulsive magnet 44 and the movable-side repulsive magnet 56 form the repulsive mechanism 78A radially inside and below the magnetic coupling mechanism 76A including the driven magnet 54 and the driving magnet 64. This enables the pump device 10A to obtain an effect similar to that of the pump device 10. In other words, the repulsive mechanism 78A forms a bearing in the radial direction of the impeller 14A, and the fixed-side repulsive magnet 44 pushes down the movable-side repulsive magnet 56 into an opposite direction of the blood inflow port 38, thereby inhibiting the impeller 14A from floating up. Moreover, as the above, the mounted position of the fixed-side repulsive magnet 44 is not specially limited, but it can be said that the fixed-side repulsive magnet 44 may be mounted in any of the pump main body 22, 22A or the drive device 24, 24A.

Second Modification Example

Figure 6:
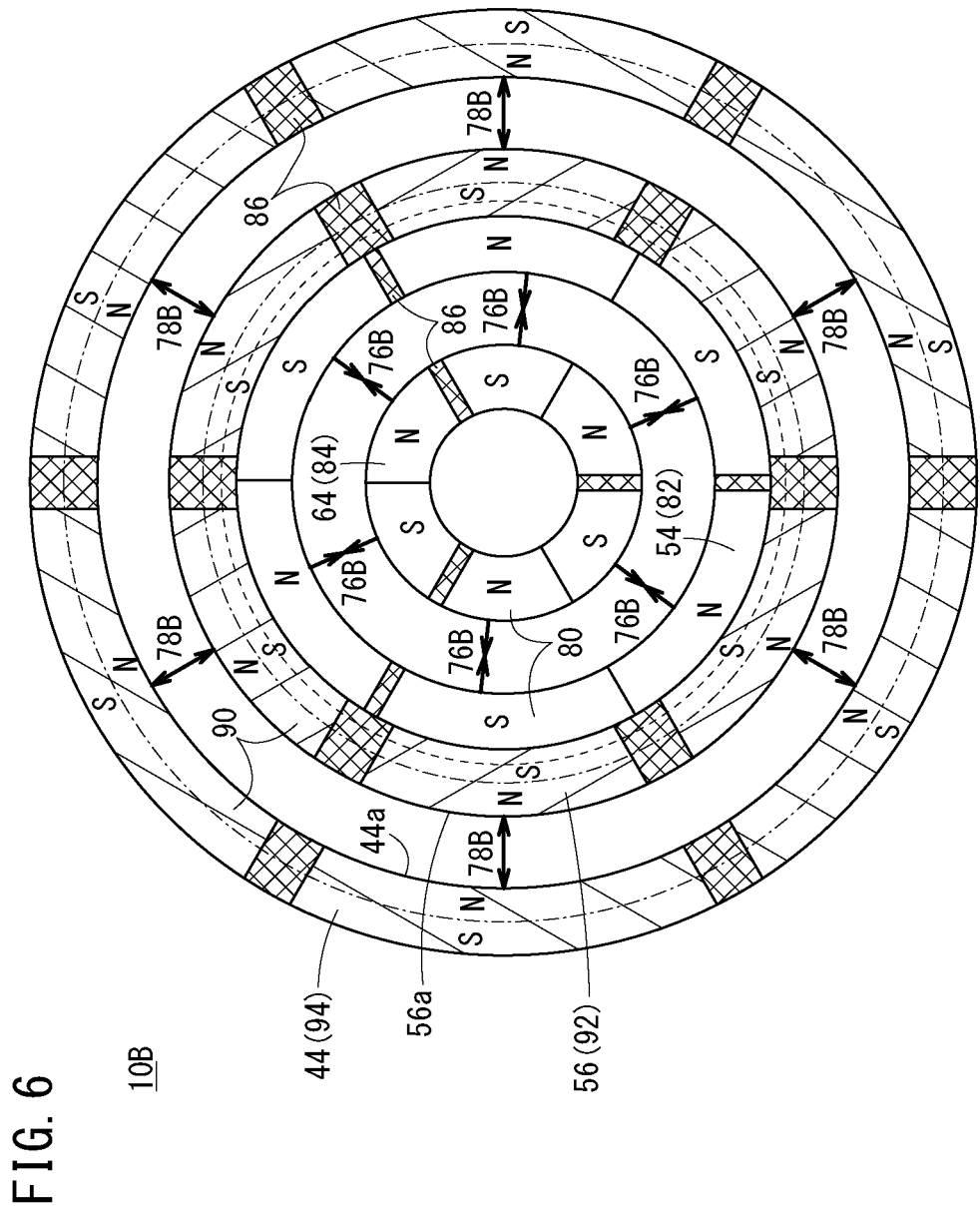
FIG. 6 is a cross-sectional view illustrating a driven magnet, a movable-side repulsive magnet, a drive magnet, and a fixed-side repulsive magnet of a pump device according to a second modification example.

A pump device 10B according to a second modification example illustrated in FIG. 6 is different from the pump device 10, 10A in that each of the fixed-side repulsive magnet 44, the driven magnet 54, the movable-side repulsive magnet 56, and the driving magnet 64 are formed as an annular magnet group in which a plurality of magnets formed in a circular arc shape are combined.

For example, in FIG. 6, as for each of the driven magnet 54 and the driving magnet 64, three circular arc-shaped magnets 80 each having the N pole and the S pole along the circumferential direction are aligned to form each of an annular driven magnet group 82 and an annular drive magnet group 84. Moreover, as for each of the movable-side repulsive magnet 56 and the fixed-side repulsive magnet 44, six circular arc-shaped magnets 90 in which the N pole and the S pole are magnetized along the circumferential direction are aligned to form each of an annular movable-side repulsive magnet group 92 and an annular fixed-side repulsive magnet group 94. Note that, in FIG. 6, each partition wall 86 is sandwiched between the magnets 80, and each partition wall 86 is sandwiched between the magnets 90, however, the partition walls 86 are not necessarily to be interposed. Moreover, the number of each of the driven magnet 54, the movable-side repulsive magnet 56, the driving magnet 64, the fixed-side repulsive magnet 44 may be designed as appropriate.

Also in the pump device 10B configured as the above, the driven magnet group 82 and the drive magnet group 84 excellently form a magnetic coupling mechanism 76B, thereby enabling the impeller 14 to be concomitantly rotated with the rotation of the motor mechanism 62. Moreover, in the pump device 10B, the movable-side repulsive magnet group 92 and the fixed-side repulsive magnet group 94 excellently form a repulsive mechanism 78B, thereby enabling the impeller 14 to rotate with stability.

Note that, the present invention is not limited to the above embodiment, but various modifications are possible along the scope of the present invention.

What is claimed is:

1. A pump device comprising:
an impeller in which a first repulsive magnet is disposed in an annular manner; and
a housing that rotatably houses therein the impeller, and includes a cylindrical inner space into which a fluid flows via an inlet port facing a vertically-oriented rotation axis of the impeller, and in which a second repulsive magnet is disposed in an annular manner;
wherein the second repulsive magnet is disposed in a position offset vertically along the rotation axis relative to the first repulsive magnet so as not to face each other radially; and
wherein the first repulsive magnet and the second repulsive magnet respectively have magnetic pole surfaces adjacent to each other with the same polarity producing a repulsive force between the first repulsive magnet and the second repulsive magnet that pushes the impeller radially inward and vertically downward around an entire circumference of the impeller.

2. The pump device according to claim 1, wherein:
the second repulsive magnet is disposed in a position offset in a radial direction orthogonal to the rotation axis at a larger radius relative to the first repulsive magnet.

3. The pump device according to claim 2, wherein:
at least one of the first repulsive magnet and the second repulsive magnet is a ring body in which a first polarity is magnetized over an entire circumference of an outer circumferential portion, and a second polarity that is an opposite polarity of the first polarity is magnetized over an entire circumference of an inner circumferential portion.

4. The pump device according to claim 1:
wherein the housing is provided with a motor mechanism configured to rotate a driving magnet; and
wherein the impeller includes a driven magnet that forms a magnetic coupling mechanism with the driving magnet therebetween, and configured to rotate the impeller together with the rotation of the driving magnet.

5. The pump device according to claim 4, wherein:
a force obtained by adding the repulsive force between the first repulsive magnet and the second repulsive magnet to a magnetic coupling force of the magnetic coupling mechanism when the first repulsive magnet and the second repulsive magnet approach each other with a predetermined distance or less therebetween is larger than a fluid force of the fluid when the impeller is rotated.

6. The pump device according to claim 4, wherein:
the repulsive force of the first repulsive magnet and the second repulsive magnet is disposed radially outward from the magnetic coupling mechanism of the driving magnet and the driven magnet.

7. The pump device according to claim 4, wherein:
the repulsive force of the first repulsive magnet and the second repulsive magnet is provided closer to the inlet port in the direction of the rotation axis than the magnetic coupling mechanism of the driving magnet and the driven magnet.

8. The pump device according to claim 4, wherein:
the first repulsive magnet and the second repulsive magnet respectively have axial lengths parallel to the rotation axis shorter than axial lengths parallel to the rotation axis of the driving magnet and the driven magnet.

9. The pump device according to claim 4:
wherein the housing includes a first sub-housing including the impeller, and a second sub-housing including the motor mechanism; and
wherein the first sub-housing and the second sub-housing are configured to be freely detachable.

10. The pump device according to claim 9, wherein:
the second repulsive magnet is disposed in the first sub-housing.

11. A blood pump for a blood circulation system, comprising:
a housing defining a chamber having a cylindrical inner space, an inlet port arranged to convey a blood flow into the chamber, and an outlet port arranged to convey blood out of the chamber;
an impeller disposed for rotation in the inner space around a vertically-oriented rotation axis to increase a pressure of the blood, wherein an upward levitation force is created on the impeller during impeller rotation at a high speed; and
a magnetic bearing for limiting inclination and levitation of the impeller within the chamber comprising a first repulsive magnet disposed annularly within the impeller and a second repulsive magnet disposed annularly within the housing, wherein the first repulsive magnet and the second repulsive magnet respectively have magnetic pole surfaces adjacent to each other having a same magnetic polarity, and wherein the second repulsive magnet is disposed in a position offset in the direction of the rotation axis toward the inlet port relative to the first repulsive magnet so as not to face each other radially, whereby a repulsive magnetic force acts on the impeller having components directed both radially inward toward the rotation axis and vertically downward away from the inlet port around a full circumference of the impeller.

12. The blood pump according to claim 11, wherein:
the second repulsive magnet is disposed in a position offset in a radial direction orthogonal to the rotation axis at a larger radius relative to the first repulsive magnet.

13. The blood pump according to claim 12, wherein:
at least one of the first repulsive magnet and the second repulsive magnet is a ring body in which a first polarity is magnetized over an entire circumference of an outer circumferential portion, and a second polarity that is an opposite polarity of the first polarity is magnetized over an entire circumference of an inner circumferential portion.

14. The blood pump according to claim 11:
wherein the housing is provided with a motor mechanism configured to rotate a driving magnet; and
wherein the impeller includes a driven magnet that forms a magnetic coupling mechanism with the driving magnet therebetween, wherein the driven magnet is configured to rotate the impeller together with the rotation of the driving magnet.

15. The blood pump according to claim 14, wherein:
a force obtained by adding the repulsive magnetic force between the first repulsive magnet and the second repulsive magnet to a magnetic coupling force of the magnetic coupling mechanism when the first repulsive magnet and the second repulsive magnet approach each other with a predetermined distance or less therebetween is larger than a fluid force of the fluid when the impeller is rotated.

16. The blood pump according to claim 14, wherein:
the repulsive magnetic force of the first repulsive magnet and the second repulsive magnet is disposed radially outward from the magnetic coupling mechanism of the driving magnet and the driven magnet.

17. The blood pump according to claim 14, wherein:
the repulsive magnetic force of the first repulsive magnet and the second repulsive magnet is provided closer to the inlet port in the direction of the rotation axis than the magnetic coupling mechanism of the driving magnet and the driven magnet.

18. The blood pump according to claim 14, wherein:
the first repulsive magnet and the second repulsive magnet respectively have axial lengths parallel to the rotation axis which are shorter than axial lengths parallel to the rotation axis of the driving magnet and the driven magnet.

* * * * *